(12) United States Patent
Harpstead

(10) Patent No.: US 6,479,066 B1
(45) Date of Patent: Nov. 12, 2002

(54) DEVICE HAVING A MICROPOROUS MEMBRANE LINED DEFORMABLE WALL FOR IMPLANTING CELL CULTURES

(75) Inventor: Stanley D. Harpstead, Arden Hills, MN (US)

(73) Assignee: RST Implanted Cell Technology, LLC, Arden Hills, MN (US)

( * ) Notice: Subject to any disclaimer, the term of this patent is extended or adjusted under 35 U.S.C. 154(b) by 0 days.

(21) Appl. No.: 09/464,560

(22) Filed: Dec. 16, 1999

(51) Int. Cl.[7] .............................. A61F 2/00; C12N 5/06; C12N 5/08; C12N 11/04; C12M 3/00
(52) U.S. Cl. ................ 424/424; 424/93.7; 424/423; 435/177; 435/180; 435/182; 435/289.1; 435/366; 435/382; 435/395; 435/402; 623/11
(58) Field of Search .................. 424/93.7, 422, 424/423, 424; 435/177, 180, 182, 39.5, 402, 289.1, 366, 382; 623/11

(56) References Cited

U.S. PATENT DOCUMENTS

| | | | |
|---|---|---|---|
| 3,946,734 A | 3/1976 | Dedrick et al. | 128/260 |
| 5,344,454 A | 9/1994 | Clarke et al. | 623/11 |
| 5,453,278 A | 9/1995 | Chan et al. | 424/422 |
| 5,545,223 A | 8/1996 | Neuenfeldt et al. | 623/11 |
| 5,569,462 A | 10/1996 | Martinson et al. | 424/424 |
| 5,593,440 A | 1/1997 | Brauker et al. | 623/11 |
| 5,653,756 A | 8/1997 | Clarke et al. | 623/11 |
| 5,688,237 A | 11/1997 | Rozga et al. | 604/53 |
| 5,713,888 A | 2/1998 | Neuenfeldt et al. | 604/891.1 |
| 5,733,336 A | 3/1998 | Neuenfeldt et al. | 623/11 |
| 5,741,330 A | 4/1998 | Brauker et al. | 623/11 |
| 5,782,912 A | 7/1998 | Brauker et al. | 633/1 |
| 5,800,529 A | 9/1998 | Brauker et al. | 623/11 |
| 5,913,998 A | 6/1999 | Butler et al. | 156/245 |

FOREIGN PATENT DOCUMENTS

| | | |
|---|---|---|
| GB | 2 020 181 A | 11/1979 |
| GB | 2 178 656 A | 2/1987 |
| WO | WO 96/36296 | 11/1996 |

*Primary Examiner*—David M. Naff
(74) *Attorney, Agent, or Firm*—Merchant & Gould, P.C.

(57) ABSTRACT

A device and method of using the device are provided for implanting cell cultures in a host. The device is formed of a deformable body, a microporous membrane and a sealable port. The shape of the body which is preferably rounded can be altered by applying stress or pressure, The body comprises a continuous wall constructed of a mesh material, and the membrane lines a surface of the body. The wall and membrane define an enclosed three-dimensional cavity for containing a cell culture. Openings of the membrane allow for passage of therapeutic substances produced by the cells and nutrients or biomolecules produced by host. The sealable port is configured for adding a cell culture to the cavity, and is formed of a material that is capable of resealing after being punctured with a needle. Because the device is deformable, it can be compressed and placed in an implantation site where it expands to conform to contours of tissue surrounding the site. The mesh may be formed of spring tempered stainless steal or memory metals. The membrane may be coated with a material such as extracellular matrix material that facilitates attachment of cells such as by ionic or covalent bonding. An external surface of the device may be coated with an angiogenic material.

24 Claims, 2 Drawing Sheets

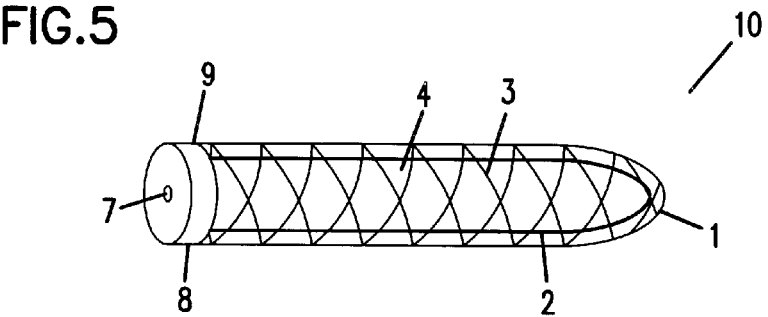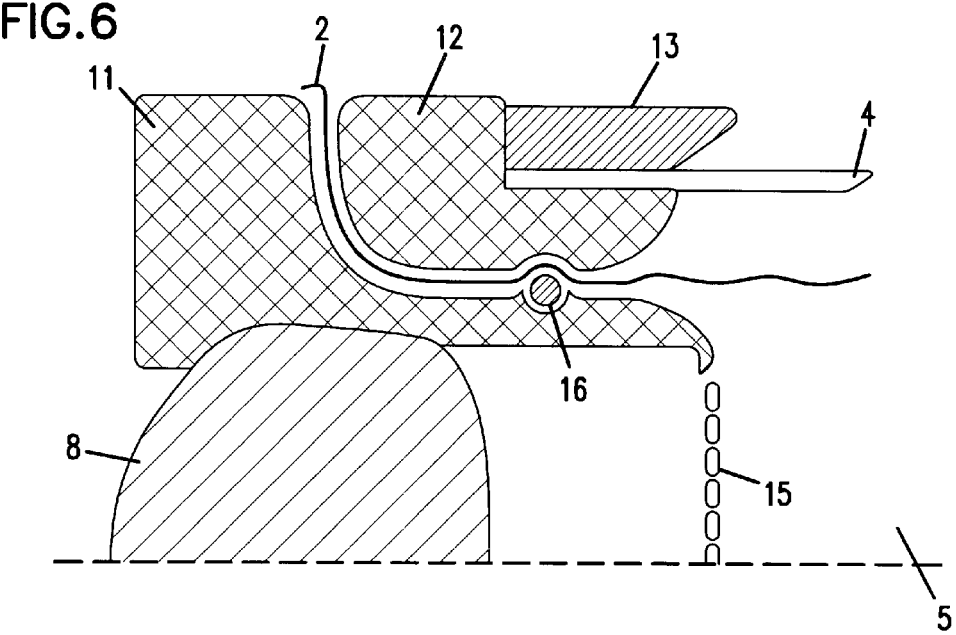

DEVICE HAVING A MICROPOROUS MEMBRANE LINED DEFORMABLE WALL FOR IMPLANTING CELL CULTURES

FIELD OF THE INVENTION

This invention relates to a device and method for implanting living cells within a host.

BACKGROUND OF THE INVENTION

It is desirable to treat various cell and molecular deficiency diseases by transferring cells into a patient having the disease. In theory, the implanted cells will generate biological products in the host that the host, because of disease or injury, cannot produce, has a deficiency, or requires for treatment, and/or modulation of a particular condition.

However, in practice, transferred cells are often rejected by the patient's immune system or become a threat to the host. Thus, the transplanted or implanted cells are not kept alive for a time sufficient to provide the intended therapeutic benefit.

Therefore, there is a need for an implant device and method which will increase the rate of successful implantation and to increase the long term viability of implanted cells.

SUMMARY OF THE INVENTION

The invention provides a device and method for implanting a cell culture in a host. The device includes a biocompatible deformable body, a biocompatible microporous membrane and a sealable port. The deformable body comprises a wall, wherein the wall defines at least one aperture. Preferably, the deformable body is in the shape of a sphere, cylinder, ovoid or ellipsoid. Preferably, the wall of the deformable body defines a plurality of apertures. In one embodiment, the wall comprises a mesh.

The biocompatible microporous membrane is supported by the deformable body such that the deformable body and microporous membrane define a cavity. The cavity is capable of containing a cell culture. Preferably the microporous membrane has openings that are sized to allow passage, for example, by diffusion, of a therapeutic substance produced by the cell culture into the host and/or to allow nutrients or biomolecules produced by the host to pass into the cavity. The microporous membrane preferably comprises a microporous polymeric material such as linear polyesters of carbonic acid, poly(vinylchloride), polyamides, styrene-acrylic acid copolymers, polysulfones, halogenated poly(vinylidene), polychloroethers, poly(urethanes) and poly(imides). In one embodiment, the microporous membrane lines an internal surface of the deformable body. In another embodiment, the microporous membrane lines an external surface of the deformable body.

The sealable port is adapted and configured for adding the cell culture to the cavity. In one embodiment, the sealable port is a sealing hub formed of a material that is capable of resealing after being punctured with a needle. Preferably, the sealing hub is formed of silicone and is maintained under pressure, for example, compressed into an aperture of the deformable body.

In one embodiment, the device can include a coating material covering a surface of the microporous membrane proximate to the cavity. Preferably, the coating material is a biologically active material that facilitates attachment of cells to the microporous membrane, for example, by ionic or covalent bonding. Examples of suitable biologically active materials include extracellular matrix molecules (ECMs), such as laminins, tenascins, collagens, netrins, semaphorin, thrombospondin, fibronectin, vitronectin, proteoglycan and biologically active fragments thereof, wherein the biologically active fragment includes a specific binding sequence of the ECM. Alternately, the biologically active material includes cell-cell adhesion molecules (CAMs), such as caherin superfamily or immunoglobulin (Ig) superfamily molecules (NCAM or fibronectins).

The invention also provides a method for implanting a cell culture in a host, administering a therapeutic substance to a host and a method of treating a disease using the device.

BRIEF DESCRIPTION OF THE FIGURES

FIG. 5 is a plan view of an embodiment of the device of the invention.

FIG. 6 is a partial enlarged cross sectional view of the device shown in FIG. 5.

DETAILED DESCRIPTION OF THE INVENTION

Figure 1:
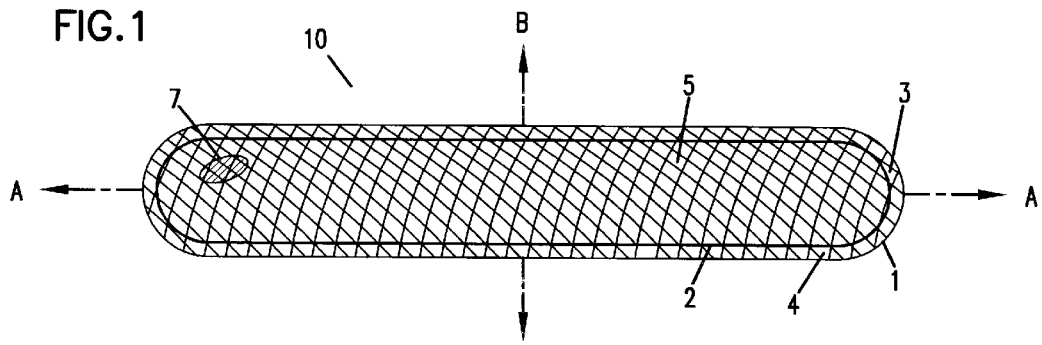
FIG. 1 is a plan view of an embodiment of the device of the invention.

The invention provides a device and method for implanting a cell culture in a host and is useful, for example, for treating cell and molecular deficiency diseases. Preferably, the implanted cells produce a therapeutic substance in the host of which the host, because of disease or injury, is in need. Advantageously, the device of the invention protects the transferred cells from attack by the host immune system, while allowing a therapeutic substance produced by the cells to diffuse into the host's tissues and/or allowing nutrients or other biological products from the host diffuse into the cell culture. The device of the invention thus allows the implanted cells to remain viable for a time sufficient to provide a therapeutic benefit. The host may be any animal, but is preferably a mammal and most typically a human. The terms "host" and "patient" are used interchangeably herein.

I. The Device

The device of the invention includes a biocompatible deformable body, a biocompatible microporous membrane and a sealable port. The device will now be described with reference to the Figures.

A. Deformable Body

The device 10 of the invention includes a deformable body 1 that defines a cavity 5. As used herein, the term "deformable body," refers to a body whose shape can be altered by applying stress or pressure to the body. For example, a deformable body 1 can be compressed, shortened, expanded, or elongated, either axially, radially or obliquely. For example, the deformable body 1 shown in FIG. 1 can be elongated along axis A—A or axis B—B. Although not necessary, it is typical that when the deformable body 1 is elongated along one axis (e.g., A—A), it is simultaneously compressed along the other axis (e.g., B—B), and vice versa. Because the device is deformable, the device can be compressed and placed in a implantation site. After placement, the device can expand to conform to the contours of tissue surrounding the implantation site. The deformable nature of the device reduces scar tissue formation as compared to other means of placement that may involve surgical formation of a pocket in the tissue.

The body 1 may be deformable because it is formed from a resilient material. As used herein, the term "resilient" refers to a material that is capable of recovering its size and shape after deformation. Preferably, the deformable body is formed using a biocompatible material. As used herein, the term "biocompatible" refers to a material that does not cause substantial tissue irritation or necrosis. Examples of biocompatible resilient materials include stainless steel and memory metals. As used herein, the term "memory metals" refers to metals that return to a particular shape at particular temperatures. The resilience of the metal is due to the crystal structure of various forms of the alloy at different temperatures. Examples of biocompatible materials include stainless steel (MP35N), titanium, tantalum, niobium. Examples of memory metals include titanium-nickel alloys, for example, Nitinol (Shape Memory Applications, Inc., NiTi, alloy code B). Alternatively, the body may be deformable due to its structure. For example, the body can be formed as a mesh, spring or other coiled and/or folded material, such as wire. In a preferred embodiment, the body is a biocompatible deformable mesh. As used herein, the term "mesh" refers to a woven material, such as a metal wire or plastic, having spaced apertures. Preferably the mesh is constructed out of spring tempered stainless steel (MP35N) with a wire diameter of 0.055 inches. Preferably, the mesh has an aperture size of about 0.05 mm to about 3.0 mm. Preferably, the aperture area is about 1 mm².

Although the deformable body 1 can be formed in any desired shape, it is preferred that the deformable body 1 is a rounded shape, such as a sphere, cylinder, ovoid or ellipsoid. A rounded shape is preferred because of the absence of pointed or sharp edges which can cause injury, discomfort and/or necrosis when the device is implanted. Additionally, a rounded shape tends to reduce the distance between the cells in the cavity and the membrane, thus reducing the distance nutrients and/or therapeutic products need to diffuse. Furthermore, a rounded shape facilitates placement within the body through a trocar, cannula or other similar device. The rounded shape also tends to distribute pressure on the host tissue equally.

Figure 3:
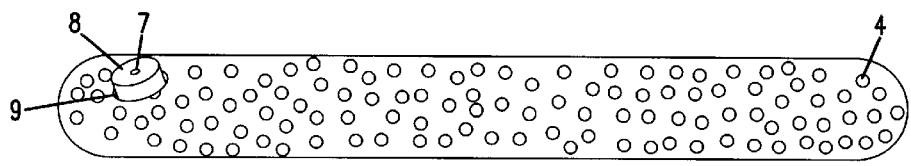
FIG. 3 is a plan view of an alternate embodiment of the device of the invention.

The deformable body 1 of the invention includes a wall 3 which defines at least one aperture 4. The apertures 4 of the deformable body 1 increase the flexibility of the deformable body 1 and also allow a therapeutic substance to diffuse into and out of the device 10. The apertures 4 can be formed as openings of a mesh (as shown in FIG. 1) or as openings in a continuous wall 3 (shown in FIG. 3). In a preferred embodiment, the apertures 4 are defined by a mesh wall 3 (shown in FIG. 1).

B. Microporous Membrane

Figure 2:
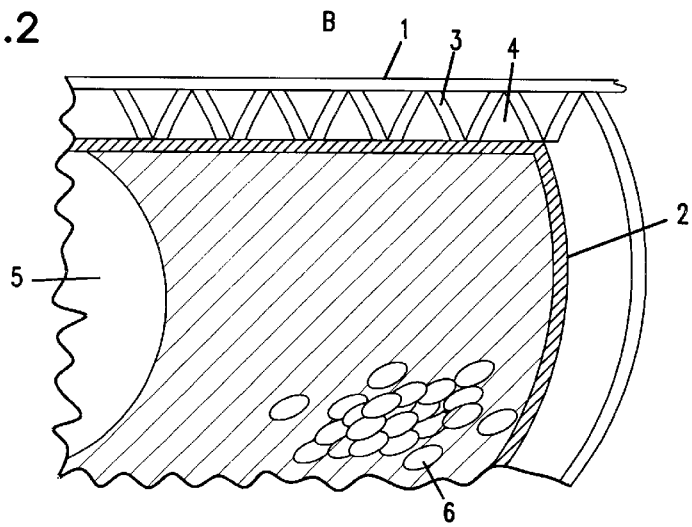
FIG. 2 is an enlarged cross sectional view of the device shown in FIG. 1.
Figure 4:
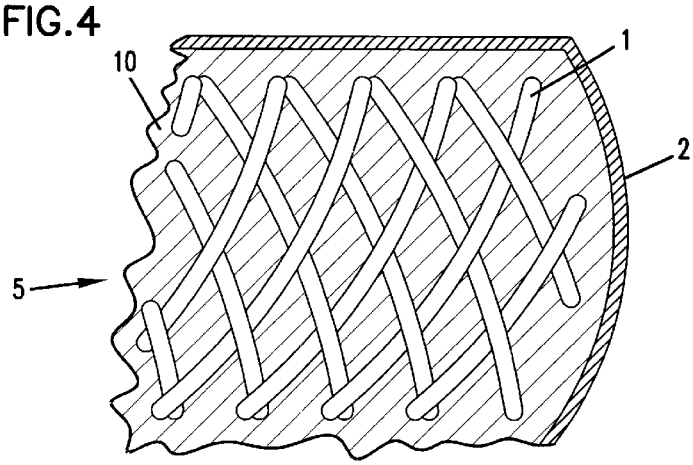
FIG. 4 is an enlarged cross sectional view of an alternate embodiment of the device shown in FIG. 1.

The device 10 of the invention also includes a biocompatible microporous membrane 2. The microporous membrane 2 is supported by the deformable body 1 such that the deformable body 1 and microporous membrane 2 together define the cavity 5. In particular, the microporous membrane 2, either alone, or in combination with the sealable port 7 or any other structure defines an enclosed cavity which surrounds and protects the cell culture from attack by the host's immune system. In one embodiment, the microporous membrane 2 lines an interior surface of the deformable body 1 (See FIGS. 1–3). In another embodiment, the microporous membrane 2 covers an external surface of the deformable body 1 (See FIG. 4).

The openings of the microporous membrane 1 are sized to allow passage, for example, by diffusion, of biomolecules (and possibly waste products) produced by the cell culture from the cavity 5 into a host and/or passage of nutrients and other biomolecules from the host into the cavity 5 of the device 10. However, the openings of the microporous membrane 1 are also sized to isolate the cell culture 6 from a host immune response, i.e., by preventing entry of immune system cells into the cavity 5. Preferably the openings are about 2 nm to about 10 nm in diameter, more preferably about 4 nm to about 6 nm. Generally, the microporous membrane comprises a microporous polymeric material such as linear polyesters of carbonic acid, poly (vinylchloride), polyamides, styrene-acrylic acid copolymers, polysulfones, halogenated poly(vinylidene), .polychloroethers, poly(urethanes) and poly(imides). The membrane preferably allows passage of macromolecules having a molecular weight of less than about 500,000 daltons, more typically less than about 100,000 daltons, most typically less than about 20,000 to 50,000 daltons. Suitable membranes include Millipore Ultrafiltration Membranes, such as Amicon High-recovery YM filters made of inert, nonionic regenerated cellulose capable of retain molecules having a nominal molecular weight greater than 1,000 to 100,000 daltons; Amicon ZM Hydrophilic Polysulfone capable of retaining molecules having a nominal molecular weight greater than 500,000 daltons; Amicon XM Polyacrylonitrile/PVC copolymer capable of retaining molecules having a nominal molecular weight greater than 50,000 to 300,000 daltons; Amicon YC Cellulose Acetate capable of retaining molecules having a nominal molecular weight greater than 500 daltons; Biomax brand filters made from polyethersulfone capable of retaining molecules having a nominal molecular weight greater than 5,000 to 50,000 daltons; Spectra/Por brand filters from Spectrum Laboratories made from regenerated cellulose or cellulose/ester capable of retaining molecules with a nominal molecular weight greater than 8,000 to 25,000 daltons; or Molecular/Por ultrafiltration membranes made of ether cellulose ester capable of retaining molecules with a nominal molecular weight greater than 100 to 500,000 daltons or polyvinylidine difluoride capable of retaining molecules with a nominal molecular weight greater than 500,000 to 1,000,000 daltons. Typically, the filters are 5 to 10 mm in diameter.

C. Sealable Port

The device 10 of the invention also includes a sealable port 7 that is adapted and configured for adding a cell culture 6 to the cavity 5 of the device 10. In one embodiment, the sealable port 7 is located within a sealing hub 8 formed of a material that is capable of resealing after being punctured with a needle. (See FIGS. 3 and 5). The sealing hub 8 is located within an aperture 9 of the wall 3 of the deformable body 1. Preferably, the sealing hub 8 is formed of silicone and is maintained under pressure. In one embodiment, the sealing hub 8 is maintained under pressure because it is compressed to fit within the aperture 9 of the wall 3 of the deformable body 1. Alternately, the sealing hub 8 can be formed from a resealable material such as silicone or polyurethane.

In one embodiment of the invention, shown in FIG. 6, the aperture 9 is defined by an enlarged wall 11 of the deformable body 1. The enlarged wall 11 is designed to maintain its shape when a sealable hub 8 is placed within the aperture 9 under pressure. The enlarged wall 11 can be formed from any suitable material that is capable of maintaining its shape, including stainless steel, titanium, polysulfone, polyurethane or ceramic. The wall 3 of the deformable body 1 can also include a secondary enlargement 12 located on an opposite side of the microporous membrane 2 as the enlarged wall 11. The enlarged wall 11 and secondary enlargement 12 can be pressed together such that the microporous membrane 2 is secured or clamped between the enlarged wall 11 and the secondary enlargement 12. In one embodiment, the enlarged wall 11 and secondary enlargement 12 are pressed together using a crimp 13. Alternately, an "O" ring 16 can be used to seal the spaces between the microporous membrane 2 and the enlarged wall 11. The "O" ring 16 can be formed from any suitable material that is compressible and biocompatible, including silicone, urethane, PTFE, and nylon.

According to the invention, a cell culture 6 can be added to the cavity 5 of the device 10 by puncturing the sealing hub 8 using a needle. Preferably, the device 10 includes a stop 15 located interior to the sealing hub which prevents the needle from puncturing the microporous membrane. More preferably, the stop 15 is perforated to allow the cell culture to pass into the cavity 5 of the device. In another embodiment, the cell culture 6 can be added to the cavity 5 of the device through the sealable port 7 into which a sealing hub 8 is subsequently inserted.

D. Adhesion Coating

In one embodiment, the device 10 of the invention can include an adhesion coating. Generally, an adhesion coating is applied to an internal surface of the microporous membrane 2 (i.e., the surface proximate the cavity 5). Preferably, the adhesion coating is a biologically active material that facilitates attachment of cells to the microporous membrane 2, for example, by ionic or covalent bonding. This is advantageous in that the diffusion distance from the cell culture to the host is shortened, thereby promoting more efficient diffusion. Examples of suitable biologically active materials include extracellular matrix molecules (ECMs), such as laminins, tenascins, collagens, netrins, and biologically active fragments thereof. An example of a "biologically active fragment" is a fragment which includes a specific binding sequence of the ECM. Alternately, the biologically active material can include cell-cell adhesion molecules (CAMs), such as caherin superfamily, fibronectins, selecting, or integrins, or immunoglobulin (Ig) superfamily molecules, such as Neural Cell Adhesion Molecule (NCAM), Liver Cell Adhesion Molecule (LCAM) or Intercellular Adhesion Molecule (ICAM).

E. Angiogenic Coating

Angiogenesis is the process of vascularization of a tissue, i.e., development of new capillary blood vessels in a tissue. Growth of blood vessels into a tissue results in improvement of oxygen and nutrient supply. Vascularization can be triggered by 'angiogenic factors' that stimulate endothelial cell proliferation and migration. Angiogenic factors are known to those of skill in the art. Examples of angiogenic factors include vascular endothelial growth factor (VEGF), Acidic fibroblast growth factor (aFGF), Basic fibroblast growth factor (bFGF), Transforming Growth Factor-Beta, Platelet-derived Endothelial Cell Growth Factor, Angiogenin and Tumor Necrosis Factor-alpha.

In one aspect of the invention, the external surface of the device 10 is coated with a composition that includes an angiogenic factor to increase the local capillary bed and improve the supply of oxygen and nutrients to the cell culture 6 within the cavity 5 of the device 10 and to improve transport of the therapeutic substance produced by the cell culture 6 from the device 10 to the host tissues.

F. Cell Culture

According to the invention, a cell culture 6 is enclosed within the cavity 5 of the device 10 of the invention. The cells can include any cell population that is capable of producing a therapeutic substance. The cells may be of a single tissue type or may contain a mixed population of cells. The cell culture may include cells that are xenogenic, allogenic and/or isogenic to the host in which they are implanted. Propagation of vertebrate cells in culture is well known in the art (See, e.g., *Tissue Culture*, Academic Press, Kruse and Patterson, editors (1973)). Examples of suitable mammalian cells include: human epithelial cells (HeLa), human embryonic kidney (HEK), Chinese hamster ovary (COS), and other known cell lines derived from tumors or from stem cells that have been developed to divide indefinitely. Cells derived from tumor cells or stem cells are preferred because they provide an unlimited source standardized, genetically homogeneous cells.

The implanted cell culture 6 may include culture media. Those of skill in the art are familiar with cell culture media. Examples of commercially available media include Ham's F10 (Sigma), Minimal Essential Medium ("MEM", Sigma), RPMI-1640 (Sigma), and Dulbecco's Modified Eagle's Medium ("DMEM", Sigma). The media may be supplemented as necessary with hormone and/or other growth factors, salts, buffers, nuclosides, antibiotices and trace elements (inorganic compounds usually present at final concentrations in the micromolar range). Alternately, the microporous membrane may allow nutrients to diffuse into the cavity to support the live cell culture.

The implanted cells preferably produce a therapeutic substance that has a beneficial effect on the host or a substance that is useful for diagnostic purposes. For example, the implanted cells can produce a therapeutic substance, in which the host is in need or deficient. The term "therapeutic substance" can refer to a low molecular weight compound, such as dopamine, or a macromolecule such as a polypeptide. Suitable polypeptides include, but are not limited to, hormones, growth factors, and enzymes of a specific biosynthetic pathway. Examples of therapeutic substances include dopamine, insulin, bone morphogenic protein (BMP)—to help repair bone fractures or as an adjunct to spinal fusion; Endorphins or Enkephalins—to activate opioid receptors; Anandamide—to activate the cannabinoid receptors, to reduce excitability of the nociceptors, or to reduce inflammation generated by mast cells; truncated forms of Calcitonin Gene Related Peptide (CGRP), for example CGRP 8–37—to reduce hyperalgesia; Insulin—to assist in the regulation of sugar levels in diabetics; Agouti protein—to antagonize the MCR4 melanocortin receptor, potentially altering feeding behavior; Neurotrophic factors such as Nerve Growth Factor (NGF), Brain Derived Neurotrophic Factor (BDNF), or Glial Derived Neurotrophic Factor (GDNF)—to help preserve nerve viability or to promote axonal elongation; and other trophic factors to help support the growth or development of body tissues.

The number of cells housed within the cavity of the device and average rate of production of a therapeutic substance per cell preferably combines to produce an overall amount of therapeutic substance sufficient to improve the patient's medical condition. The amount of therapeutic substance necessary to effect clinically significant improvement in the medical condition of a patient depends upon several factors including the severity of the medical condition and the medical condition being treated. Such factors are known to those of skill in the art.

G. Transformed Cells

In one embodiment of the invention the implanted cells can be genetically engineered transformed cells. As used herein, the term "transformed cells" refers to cells in which an extrinsic DNA or gene construct has been introduced such that the DNA is replicable, either as an extrachromosomal element or by chromosomal integration. Transformation of the cells is accomplished using standard techniques known to those of skill in the art and is described, for example, by Sambrook et al., *Molecular Cloning: A Laboratory Manual, New York*, Cold Spring Harbor Laboratory Press, 1989.

Extrinsic DNA or gene construct refers to a nucleic acid sequence originating outside a recipient cell and introduced into a recipient cell by a DNA delivery technique. A DNA or gene construct may be manufactured using recombinant DNA technology known in the art, or may be a nucleic acid fragment purified from a source material. The extrinsic gene may be entirely composed of homologous sequence, i.e., sequences cloned, isolated, or derived from the same species from which the recipient cells derive. Alternatively, all or a portion of the extrinsic gene may be composed of sequences from species other than the species from which the recipient cells derive, hereinafter termed heterologous sequences. The extrinsic gene construct may be natural in that none of the regulatory sequences and coding sequences that may be a part of the gene are substantially or intentionally altered, or the extrinsic gene construct may be chimeric in that sequence fragments from various sources are present in the final gene construct.

It is envisioned that the "transformed cells" would be designed to preferentially interact with an "adhesion coating" of biologically active material on the internal surface of the microporous membrane. This interaction may facilitate adhesion to the inner surface of the microporous membrane to enhance diffusion kinetics, or, through activation of intracellular kinase or phosphate enzymatic cascades, lead to an increase or decrease in the transcription, translation, intracellular transport or exocytosis of the "therapeutic substance".

II. The Method

The invention also provides a method for implanting a cell culture in a host, administering a therapeutic substance to a host and a method of treating a disease. According to the invention, a cell culture 6 can be implanted into a host by introducing the cell culture 6 into the cavity 5 of the device 10 of the invention and then implanting the device 10 into a host. This method can also be used to administer a therapeutic substance to a host or to treat a disease.

The device may be implanted into a host intraperiotoneally, intramuscularly, intrathecally, intraventricularly, into the bone marrow within the lumen of the bone, or subcutaneously, as desired. The implantation site may depend upon the nature of the particular medical condition to be treated. Generally, the implantation site is not critical to the practice of the invention provided that the site is capable of supporting vascularization. Preferred sites include, but are not limited to, intraperitoneal fat sites, the omentum, various subcutaneous sites, intervertebral discs and bone marrow. The present device is able to create its own required space in the tissue of the host after being implanted.

Those of skill in the art are familiar with method of implanting devices in a patient. In a preferred embodiment, the device is implanted through the lumen of a trocar. The cells may be placed in the device either before or after implantation. In addition, additional culture or nutrient can be supplied after implantation through the sealable port.

While a detailed description of the invention has been provided above, the invention is not limited thereto, and modifications not departing from the spirit or scope of the invention will be apparent. The invention is defined by the following claims.

What is claimed is:

1. A device for implanting a cell culture in a host, comprising:
   a. a biocompatible deformable body whose shape can be altered by applying stress or pressure, said body comprising a continuous wall constructed from a mesh material,
   b. a biocompatible microporoas membrane lining a surface of the deformable body, wherein the continuous wall and biocompatible microporous membrane define an enclosed three-dimensional cavity; and
   c. a sealable port adapted and configured for adding a cell culture to the enclosed three-dimensional cavity, wherein the sealable port is formed of a material that is capable of resealing after being punctured with a needle.

2. The device of claim 1, wherein the deformable body is formed from a material selected from the group consisting of stainless steel and memory metals.

3. The device of claim 1, further comprising a coating material covering a surface of the microporous membrane that is proximate the cavity.

4. The device of claim 3, wherein the coating material is a biologically active material.

5. The device of claim 4, wherein the biologically active material-is attached to the membrane by ionic or covalent bonding.

6. The device of claim 5, wherein the biologically active material facilitates attachment of cells to the microporous membrane.

7. The device of claim 5, wherein the biologically active material is an extracellular matrix molecule.

8. The device of claim 7, wherein the extracellular matrix molecule is selected from the group consisting of laminin, tenascin, collagen, netrin, semaphorin, thrombospondin, fibronectin, vitronectin, proteoglycan and biologically active fragments thereof.

9. The device of claim 8, wherein the biologically active fragment includes a extracellular matrix binding sequence.

10. The device of claim 5, wherein the biologically active material includes cell-cell adhesion molecules.

11. The device of claim 10, wherein the cell-cell adhesion molecule is selected from the group consisting of caherin superfamily and immunoglobulin (Ig) superfamily molecules.

12. The device of claim 1, wherein the microporous membrane comprises a microporous polymeric material.

13. The device of claim 1, wherein the microporous polymeric material is selected from the group consisting of linear polyesters of carbonic acid, poly(vinylchloride), polyamides, styrene-acrylic acid copolymers, polysulfones, halogenated poly(vinylidene), polychloroethers, poly(urethanes) and poly(imides).

14. The device of claim 1, wherein the microporous membrane lines an interior surface of the deformable body.

15. The device of claim 1, wherein the microporous membrane lines an external surface of the deformable body.

16. The device of claim 1, wherein the deformable body is a cylinder, sphere or ovoid.

17. The device of claim 1, wherein the sealable port is formed from a material selected from the group consisting of silicone and polyurethane.

18. The device of claim 17, wherein the sealable port includes silicone and is maintained under pressure.

19. The device of claim 1, further comprising means for preventing- a needle from penetrating the microporous membrane.

20. The device of claim 1, wherein the cell culture includes a mammalian cell culture selected from the group consisting of human epithelial cells (HeLa), human embryonic kidney cells (HEK), and Chinese hamster ovary cells (COS).

21. The device of claim 1, wherein the cell culture includes cells that are genetically modified.

22. The device of claim 21, wherein the cells are genetically modified to present a complementary cell-cell adhesion molecule on their plasma membrane.

23. The device of claim 1, wherein cells in the cell culture are activated upon binding to the microporous membrane, said activation resulting in release of vesicle contents, increase in transcription of a desired gene, increase in translation of MRNA, facilitation of post-translational splicing, increase in vesicle loading or facilitation of vesicle positioning or processing to a desired gene product.

24. The device of claim 23, wherein activation of the cells occurs due to activation of cell adhesion molecules expressed on a plasma membrane of the cell.

* * * * *